(12) United States Patent  (10) Patent No.: US 8,491,543 B2
Stringham  (45) Date of Patent: *Jul. 23, 2013

(54) AUTOMATIC SAFETY OCCLUDER

(75) Inventor: Mark Stringham, Salt Lake City, UT (US)

(73) Assignee: Zevex, Inc., Salt Lake City, UT (US)

( * ) Notice: Subject to any disclaimer, the term of this patent is extended or adjusted under 35 U.S.C. 154(b) by 90 days.

This patent is subject to a terminal disclaimer.

(21) Appl. No.: 13/188,818

(22) Filed: Jul. 22, 2011

(65) Prior Publication Data
US 2011/0276000 A1 Nov. 10, 2011

Related U.S. Application Data

(62) Division of application No. 12/701,467, filed on Feb. 5, 2010, now Pat. No. 7,998,121.

(60) Provisional application No. 61/150,705, filed on Feb. 6, 2009.

(51) Int. Cl.
A61M 5/00 (2006.01)
A61M 1/00 (2006.01)

(52) U.S. Cl.
USPC ............... 604/250; 604/151; 251/4; 251/6

(58) Field of Classification Search
USPC .......... 604/118, 246, 249, 250–251; 251/4–5, 251/7, 90, 321, 337
See application file for complete search history.

(56) References Cited

U.S. PATENT DOCUMENTS

| 584,091 | A | 6/1897 | Leidich |
| 1,238,521 | A | 8/1917 | Janish, Jr. |
| 2,471,623 | A | 5/1949 | Hubbell |
| 2,518,165 | A | 8/1950 | Millard |
| 2,858,095 | A | 10/1958 | Harris et al. |
| 2,999,499 | A | 11/1961 | Willet |
| 3,213,882 | A | 10/1965 | Beatty |
| 3,329,391 | A | 7/1967 | Deane |
| D208,753 | S | 9/1967 | Curry |
| 3,497,175 | A | 2/1970 | Koland |
| 3,707,972 | A | 1/1973 | Villari et al. |
| 3,985,140 | A | 10/1976 | Harris |
| 3,998,364 | A | 12/1976 | Hollander |

(Continued)

FOREIGN PATENT DOCUMENTS

| EP | 0 150 666 | 9/1984 |
| EP | 0 276 356 | 8/1988 |

(Continued)

OTHER PUBLICATIONS

International Preliminary Report on Patentability, issued Aug. 18, 2011 in related PCT Patent Application No. PCT/US2010/023409.

Primary Examiner — Quynh-Nhu H Vu
(74) Attorney, Agent, or Firm — Hodgson Russ LLP

(57) ABSTRACT

An automatic safety occluder provides an occluder for an infusion set that is biased in a closed position until an electrical signal is received that causes the occluder to open. Should the occluder fail to be installed correctly, or if power is removed, the occluder will return to its biased closed position, preventing free flow. The occluder may also be placed in an integrated unit such that the automatic safety occluder may attach to the tubing as a unit.

3 Claims, 7 Drawing Sheets

U.S. PATENT DOCUMENTS

| | | |
|---|---|---|
| 4,037,596 A | 7/1977 | LeFevre et al. |
| 4,063,555 A | 12/1977 | Ulinder |
| 4,065,093 A | 12/1977 | Phillips |
| 4,106,675 A | 8/1978 | Taylor |
| 4,142,645 A | 3/1979 | Walton |
| 4,160,383 A | 7/1979 | Rauschenberger |
| 4,230,151 A | 10/1980 | Jonsson |
| 4,236,880 A | 12/1980 | Archibald |
| 4,300,571 A | 11/1981 | Waldbillig |
| 4,373,524 A | 2/1983 | Leibinsohn |
| 4,381,591 A | 5/1983 | Barger et al. |
| 4,382,453 A | 5/1983 | Bujan et al. |
| 4,425,116 A | 1/1984 | Bilstad et al. |
| 4,430,073 A | 2/1984 | Bemis et al. |
| 4,453,295 A | 6/1984 | Laszczower |
| 4,498,843 A | 2/1985 | Schneider et al. |
| 4,524,802 A | 6/1985 | Lawrence et al. |
| 4,527,588 A | 7/1985 | Tseo et al. |
| 4,559,036 A * | 12/1985 | Wunsch .................. 604/81 |
| 4,559,045 A | 12/1985 | Danby et al. |
| 4,579,553 A | 4/1986 | Urquhart et al. |
| 4,596,557 A | 6/1986 | Pexa |
| 4,624,663 A | 11/1986 | Danby et al. |
| 4,634,092 A | 1/1987 | Daniell et al. |
| 4,645,489 A | 2/1987 | Krumme et al. |
| 4,689,043 A | 8/1987 | Bisha |
| 4,728,324 A | 3/1988 | Steigerwald et al. |
| 4,730,635 A | 3/1988 | Linden |
| 4,787,406 A | 11/1988 | Edwards et al. |
| 4,913,401 A | 4/1990 | Handke |
| 4,932,629 A | 6/1990 | Rodomista et al. |
| 4,932,938 A | 6/1990 | Goldberg et al. |
| 4,935,010 A | 6/1990 | Cox et al. |
| 4,960,259 A | 10/1990 | Sunnanvader et al. |
| 5,017,192 A | 5/1991 | Dodge et al. |
| 5,020,562 A | 6/1991 | Richmond et al. |
| 5,022,422 A | 6/1991 | di Palma |
| 5,029,621 A | 7/1991 | Lewis |
| 5,083,561 A | 1/1992 | Russo |
| 5,098,406 A | 3/1992 | Sawyer |
| 5,151,019 A | 9/1992 | Danby et al. |
| 5,219,327 A | 6/1993 | Okada |
| 5,232,193 A | 8/1993 | Skakoon |
| 5,238,218 A | 8/1993 | Mackal |
| 5,254,083 A | 10/1993 | Gentelia et al. |
| 5,257,978 A | 11/1993 | Haber et al. |
| 5,265,847 A | 11/1993 | Vorhis |
| 5,336,174 A | 8/1994 | Daoud et al. |
| 5,351,932 A | 10/1994 | Von Herrmann |
| 5,391,144 A * | 2/1995 | Sakurai et al. .................. 604/22 |
| 5,395,351 A | 3/1995 | Munsch |
| 5,396,925 A | 3/1995 | Poli |
| 5,437,642 A | 8/1995 | Thill et al. |
| 5,438,868 A | 8/1995 | Holden et al. |
| 5,456,887 A | 10/1995 | Calvo et al. |
| 5,474,544 A | 12/1995 | Lynn |
| 5,482,446 A | 1/1996 | Williamson et al. |
| 5,514,102 A | 5/1996 | Winterer et al. |
| 5,531,680 A | 7/1996 | Dumas et al. |
| 5,531,713 A | 7/1996 | Mastronardi et al. |
| 5,556,386 A | 9/1996 | Todd |
| 5,578,070 A | 11/1996 | Utterberg |
| D389,228 S | 1/1998 | Winterer et al. |
| 5,704,584 A * | 1/1998 | Winterer et al. .................. 251/7 |
| 5,720,721 A | 2/1998 | Dumas et al. |
| 5,733,061 A | 3/1998 | Child |
| 5,746,756 A | 5/1998 | Bromfield et al. |
| 5,789,675 A | 8/1998 | Blaine et al. |
| 5,807,312 A | 9/1998 | Dzwonkiewicz |
| 5,810,323 A | 9/1998 | Winterer et al. |
| 5,826,621 A | 10/1998 | Jemmott |
| 5,971,357 A | 10/1999 | Denton et al. |
| 6,017,332 A | 1/2000 | Urrutia |
| 6,023,970 A | 2/2000 | Blaine |
| 6,048,331 A | 4/2000 | Tsugita |
| 6,092,695 A | 7/2000 | Loeffler |
| 6,142,979 A | 11/2000 | McNally et al. |
| RE37,074 E | 2/2001 | Danby et al. |
| 6,183,447 B1 | 2/2001 | Urrutia |
| 6,192,752 B1 | 2/2001 | Blaine |
| 6,196,922 B1 | 3/2001 | Hantschk et al. |
| 6,196,992 B1 | 3/2001 | Keilman et al. |
| 6,209,538 B1 | 4/2001 | Casper et al. |
| 6,261,262 B1 | 7/2001 | Briggs et al. |
| 6,328,720 B1 | 12/2001 | McNally et al. |
| D455,489 S | 4/2002 | Beck et al. |
| 6,398,758 B1 | 6/2002 | Jacobsen et al. |
| 6,398,780 B1 | 6/2002 | Farley et al. |
| 6,461,335 B1 | 10/2002 | Noecker |
| 6,494,864 B1 | 12/2002 | Kerwin et al. |
| 6,506,035 B1 | 1/2003 | Beck |
| 6,523,414 B1 | 2/2003 | Malmstrom et al. |
| 6,531,708 B1 | 3/2003 | Malmstrom et al. |
| RE38,145 E | 6/2003 | Lynn |
| 6,595,950 B1 | 7/2003 | Miles et al. |
| 6,623,447 B2 | 9/2003 | Miles et al. |
| 6,636,010 B1 | 10/2003 | Malmstrom et al. |
| H2090 H | 11/2003 | Walker |
| 6,659,976 B2 | 12/2003 | Beck et al. |
| 6,685,670 B2 | 2/2004 | Miles et al. |
| 6,749,591 B1 | 6/2004 | McNally et al. |
| 6,750,468 B2 | 6/2004 | Malmstrom et al. |
| D501,924 S | 2/2005 | Cise et al. |
| 6,852,094 B2 | 2/2005 | Beck et al. |
| D503,799 S | 4/2005 | Beck |
| D503,978 S | 4/2005 | Beck |
| D504,506 S | 4/2005 | Beck et al. |
| D505,199 S | 5/2005 | Beck et al. |
| 6,902,541 B2 | 6/2005 | McNally et al. |
| 6,907,788 B2 | 6/2005 | Malmstrom et al. |
| D507,647 S | 7/2005 | Beck et al. |
| 6,923,785 B2 | 8/2005 | Miles et al. |
| 6,949,376 B2 | 9/2005 | Kluttz et al. |
| 6,979,311 B2 | 12/2005 | Miles et al. |
| 7,037,302 B2 | 5/2006 | Vaillancourt |
| D523,553 S | 6/2006 | Beck et al. |
| 7,070,575 B2 | 7/2006 | Beck et al. |
| 7,121,143 B2 | 10/2006 | Malmstrom et al. |
| 7,150,727 B2 | 12/2006 | Cise et al. |
| D536,783 S | 2/2007 | Cise et al. |
| 7,367,963 B2 | 5/2008 | Cise et al. |
| 7,998,121 B2 * | 8/2011 | Stringham .................. 604/250 |
| 2002/0169424 A1 | 11/2002 | Miles et al. |
| 2004/0220542 A1 | 11/2004 | Cise et al. |
| 2004/0260332 A1 | 12/2004 | Dubrul et al. |
| 2005/0004540 A1 | 1/2005 | McNally |
| 2005/0119625 A1 | 6/2005 | Miles et al. |
| 2006/0058740 A1 | 3/2006 | Cise |
| 2007/0118078 A1 | 5/2007 | McNally |
| 2007/0151346 A1 | 7/2007 | Malmstrom et al. |
| 2008/0065008 A1 | 3/2008 | Barbut et al. |
| 2008/0098798 A1 | 5/2008 | Riley |
| 2008/0103445 A1 | 5/2008 | Blaine et al. |
| 2008/0119782 A1 | 5/2008 | Steinman |
| 2008/0134750 A1 | 6/2008 | Riley |
| 2008/0208117 A1 | 8/2008 | Steinman |
| 2008/0276911 A1 | 11/2008 | Woody |
| 2009/0049919 A1 | 2/2009 | Hills |
| 2009/0149801 A1 | 6/2009 | Crandall |
| 2009/0254034 A1 | 10/2009 | Beck |

FOREIGN PATENT DOCUMENTS

| | | |
|---|---|---|
| EP | 0 423 978 | 10/1990 |
| EP | 0 483 794 | 10/1991 |
| GB | 2 338 759 | 12/1999 |
| WO | WO 96/08666 | 3/1996 |
| WO | WO 96/17636 | 6/1996 |

* cited by examiner

US 8,491,543 B2

AUTOMATIC SAFETY OCCLUDER

PRIORITY

The present application is a divisional of U.S. Pat. No. 12/701,467, filed Feb. 5, 2010, now U.S. Pat. No. 7,998,121, and claims the benefit of U.S. Provisional Application Ser. No. 61/150,705, filed Feb. 6, 2009, which are herein incorporated by reference in their entirety.

THE FIELD OF THE INVENTION

The present invention relates to an apparatus and method for selectively preventing and allowing free flow of solutions through a tube. More particularly, the present invention relates to preventing free flow of solutions while administering fluids to a patient such as during I.V. infusion or during enteral or parenteral administration of solutions through an infusion line. More particularly, the present invention relates to an occluder/valve and method of use for infusion sets and the like, wherein the occluder/valve automatically prevents undesirable free-flow of solution through the infusion set while allowing an electrical signal to place the infusion set in a free-flow condition to facilitate the rapid delivery of fluids to a patient.

BACKGROUND

The use of infusion sets to administer solutions to patients is well known in the medical arts. Infusion sets are used for I.V. infusion as well as enteral and parenteral applications, for example. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump or an IV pump, is placed along the infusion set to control the rate at which the solution is fed to the patient. In applications where a pump, etc., is used, the clamp used to control the flow of the solution (if present on the infusion set) is typically opened to its fullest extent to prevent the clamp from interfering with the proper functioning of the pump. The clamp is opened with the expectation that the enteral feeding pump will control fluid flow through the infusion set. However, emergencies or other distractions may accidentally remove the infusion set from the pump or prevent the medical personnel from properly loading the infusion set in the enteral feeding pump.

When the infusion set is not properly loaded in the pump and the clamp has been opened, a situation known as free-flow often develops. The force of gravity or a pressure differential causes the solution to flow freely into the patient unchecked by the pump or other regulating device. Under a free-flow condition, an amount of solution many times the desired dose can be supplied to the patient within a relatively short time period. This can be particularly dangerous if the solution contains medicine as this could result in an overdose of medication. Free flow can also be dangerous where the patient's body is not physically strong enough to adjust to the large inflow of solution. There have been numerous occasions in which a patient has died due to the over-infusion of fluid during a given amount of time. Thus, preventing an undesirable free-flow state is highly desirable.

Numerous devices have been developed in an attempt to prevent free flow conditions. Such devices, however, add to the overall cost of the infusion set and some provide only marginal protection against free flow. Others may have other limitations which limit the usefulness of the occluder.

One popular anti-free flow occluder is described in U.S. Pat. No. 5,704,584 (Winterer et al.). The '584 patent teaches an occluder which is disposed around the outside of an infusion set to selectively prevent fluid flow. The occluder is biased into a closed position wherein the occluder stops flow through the infusion set. The biasing can be overcome by manually holding the occluder open, or by mounting the occluder in a pump and then closing a door so that the door holds the occluder open. The '584 patent describes the general use of occluders in infusion pumps.

While preventing unintended free-flow situations is important, there are also times in which a free-flow condition is desired. This may be the case where a patient's heart has stopped or in other emergency situations where quick corrective action is desired. Often medicines will be injected into an IV solution being administered to the patient with the desire that the solution and medicine enter the patient as quickly as possible. If the infusion set uses one of the above referenced occluders, the medical staff must ensure that free-flow conditions are being allowed. This may mean removing the infusion set from the pump in which it is housed and manually holding open the occluder. Obviously, this is not desirable, as each member of the medical staff has important duties during an emergency situation. Thus, it is desirable for medical staff to be able to lock the occluder open in an emergency or other situation in which a free-flow condition is specifically desired.

Several types of occluders can be locked in an open position. One such occluder is biased closed and designed to accept a pin into a pair of apertures to hold the occluder in an open position. Such occluders, however, are disadvantageous because the pin can be lost during the commotion involved with an emergency and the occluder may be left in a biased closed condition.

Another known occluding system uses a spring which is biased to pinch closed the tubing of an infusion set. The spring can be pushed into an open position where it allows flow through the infusion set by pressing down on a locking trigger. The locking trigger can also be moved into a locked position wherein the spring is held in an open position. The occluding system, however, is disadvantageous, as it is relatively bulky. Additionally, if the trigger is disposed in the locked open position, the module cannot be properly loaded into a pump, as the pump door will not close.

There is a need for an occluder which allows for greater control and flexibility in selecting an open or closed occluder position. There is a need for an occluder which may be controlled electronically as well as mechanically, allowing a pump or other device attached to the occluder to selectively allow or prevent flow through an infusion tube. There is a need for an occluder which automatically occludes flow through a tube if power is lost or if the tubing set is removed from the pumping device, preventing the uncontrolled flow of fluids in such a situation. There is also a need for such an occluder which is relatively inexpensive and which is easy to use.

SUMMARY OF THE INVENTION

It is an object of the present invention to provide an apparatus and method for selectively occluding infusion sets to prevent an accidental or undesired free-flow condition, and which can be automatically placed in the off position if power is lost.

According to one aspect of the invention, an occluder is provided which uses an electrical solenoid to operate the occluder. The occluder is biased into an occluding position by a spring internal to the occluder and uses the solenoid to move the occluder into an open position. An electrical signal from an infusion pump or other associated equipment will cause the occluder to open and remain open as is desired. Should the electrical signal stop, the occluder will return to its biased closed position automatically.

These and other aspects of the present invention are realized in an automatic safety occluder as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single FIGURE, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
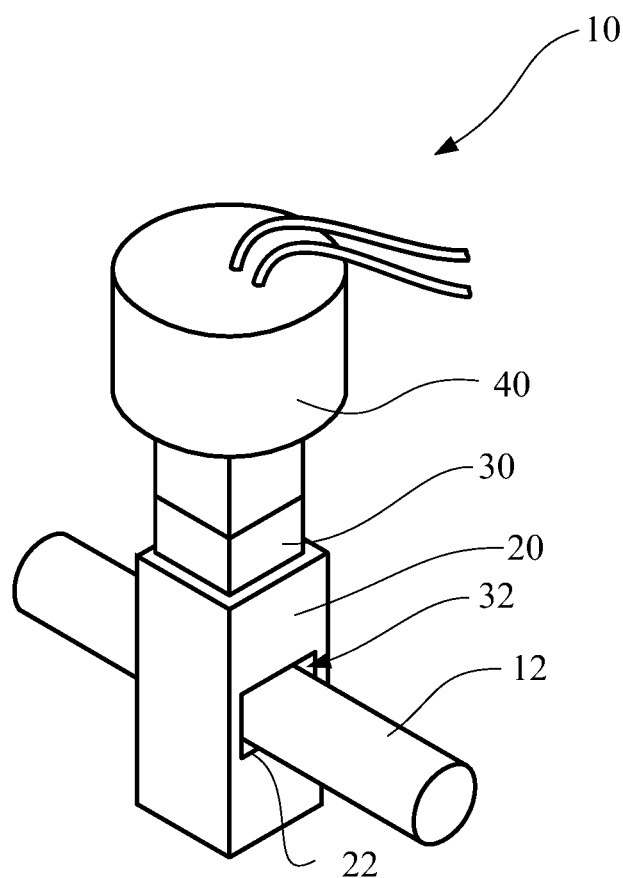
FIG. 1 shows a perspective view of an automatic safety occluder.

Turning now to FIG. 1, a perspective view of an occluder 10 disposed upon a piece of tubing 12 of an infusion set is shown. The infusion tubing 12 is for carrying a fluid to a patient, and also includes connectors and other necessary parts. If used in an infusion pump, the infusion set may often include an upstream tube connectable to a fluid reservoir, a pump engaging section of tubing 12, and a downstream tube which is connected to the patient. The pump engaging tubing is connected to the upstream and downstream tubing, and is typically a more resilient tubing that functions better in a pump and occluder 10. The occluder 10 includes a body 20, plunger 30 and actuator 40. The body 20 and plunger 30 have apertures 22 and 32 therethrough, and the tubing 12 passes through the passages 22 and 32. When the plunger 30 is pressed into the body 20, the apertures 22 and 32 are aligned (as shown), allowing flow through the tube 12. A spring presses the plunger away from the body, causing the apertures 22, 32 to become misaligned and causing the tubing to be pinched between the walls forming the apertures.

The actuator 40 is an electrical solenoid. The solenoid 40 and/or plunger 30 is biased into a closed position which misaligns the apertures 22, 32 and prevents flow, typically by a compression spring disposed in the body of the occluder 10. As such, when the solenoid 40 is not receiving an electrical signal, the solenoid 40 allows the plunger 30 and body 20 to pinch the tubing 12 closed. The solenoid 40 may have a spring therein to bias the solenoid into a non-actuated position such that the friction involved with actuating the solenoid does not interfere with the operation of the occluder 10. When the solenoid 40 receives an electrical signal to open, it presses on the plunger 30 and causes the body aperture 22 and plunger aperture 32 to align and thereby cease pinching the tubing 12 closed. Should the power be removed from the solenoid 40, the body 20 and plunger 30 will return to their biased closed state.

According to one aspect of the invention, the piston of the solenoid 40 may be attached to the plunger 30 and the solenoid 40 is not attached to the body of the occluder 20. When the infusion set and occluder 10 are loaded in an infusion pump (60, FIG. 7), the body of the solenoid 40 is disposed adjacent a retaining structure in the pump, such as a wall. Thus, when an electrical signal is applied to the solenoid 40, the solenoid expands and presses against the pump body (i.e. the retaining wall) and the plunger 30, allowing flow through the occluder 10. If the occluder 10 and solenoid 40 are removed from the pump, the occluder 10 is closed regardless of whether electricity is applied to the solenoid, since only the solenoid piston and not the solenoid body is connected to the occluder.

According to another aspect of the invention, the solenoid 40 may be part of the infusion pump 60. The plunger 30 is then disposed adjacent the solenoid 40 when the infusion set and occluder 10 are loaded into the pump, allowing actuation of the solenoid to actuate the occluder 10 by compressing the occluder plunger 30. The solenoid 40 presses against the plunger 30 when an electrical signal is applied to the solenoid 40. Again, the occluder 10 is closed if removed from the pump since the solenoid 40 remains as part of the pump. Similarly, should the plunger 30 or body 20 be incorrectly installed relative to the solenoid 40, the automatic safety occluder 10 will remain biased in the closed state.

The use of the occluder 10 in combination with a solenoid 40 is advantageous for several reasons. Prior occluders allowed flow through the tubing once the infusion set was mounted into the pump, regardless of the operational state of the pump. The present occluder 10 and solenoid 40 allows the pump electronics to control the operation of the occluder beyond the simple mounting state of the occluder. Thus, if flow must be stopped due to a pump error or air bubbles in the solution, the pump 60 may close the occluder 10 to prevent flow by removing any electrical signal from the solenoid 40. The occluder 10 may thus be closed faster than the pump 60 may stop. This makes the occlduer 10 more reliable in preventing flow through the tubing 12.

Figure 2:
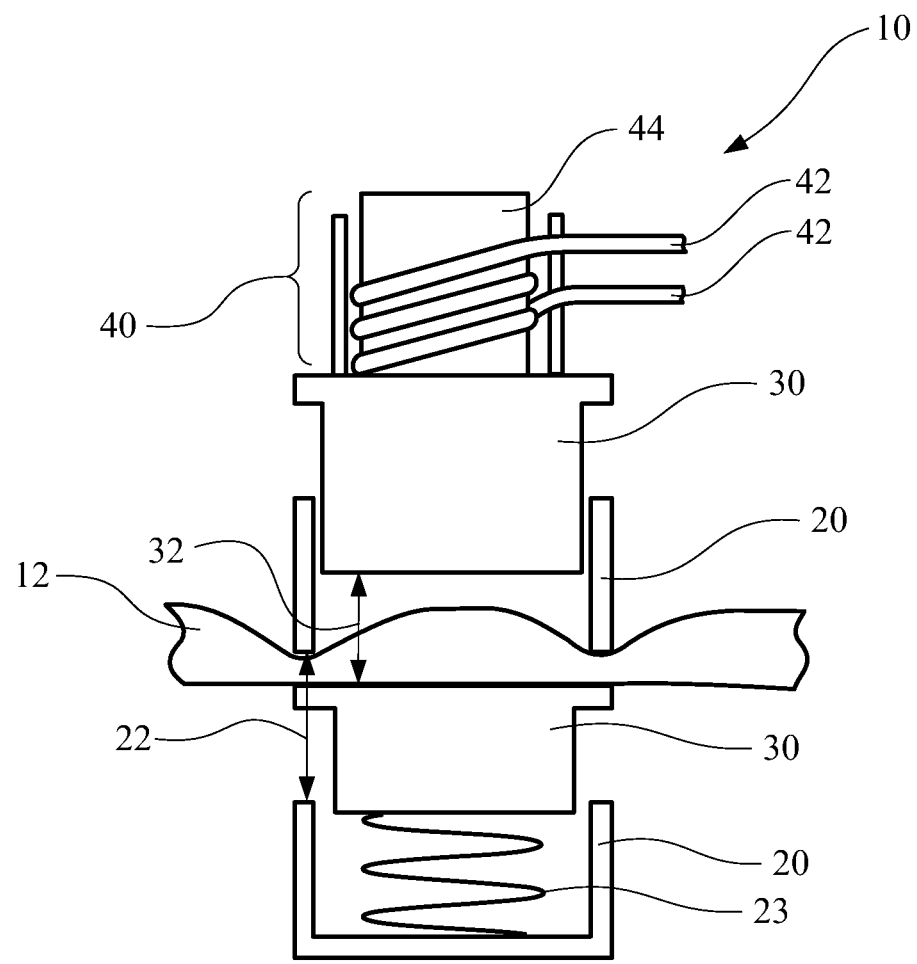
FIG. 2 shows a partially cut away view of the automatic safety occluder of FIG. 1 in its biased closed condition.

Turning now to FIG. 2, a cut away view of the occluder 10 in its biased closed state is shown. When the solenoid 40 is not active, a spring 23 biases the plunger 30 upwardly, pinching the tubing 12 between the plunger 30 and the body 20 and preventing flow within the tubing 12. Typically, the occluder 10 uses a conventional push-type solenoid 40 to actuate the occluder. Such a solenoid extends a piston 44 therefrom when an electrical signal is applied to the solenoid and contains an internal spring to retract the piston 44 in the absence of an electrical signal. When the solenoid 40 is not receiving an electrical signal, the solenoid piston 44 is retracted into the solenoid body and away from the occluder body 20 and plunger 30, allowing the spring 23 to pinch the tubing 12 closed. The lack of signal may be deliberate, as in a desire to close the automatic safety occluder, or by mistake, such as an accidental breaking of the signal wires 42. In such an arrangement, the occluder 10 provides additional safety in that it fails into a closed position should there a problem with the solenoid control wires. Similarly, a push-pull solenoid may be used where open and closed positions are actively driven, but should a failure occur, the automatic safety occluder 10 will return to the closed position due to the bias.

Figure 3:
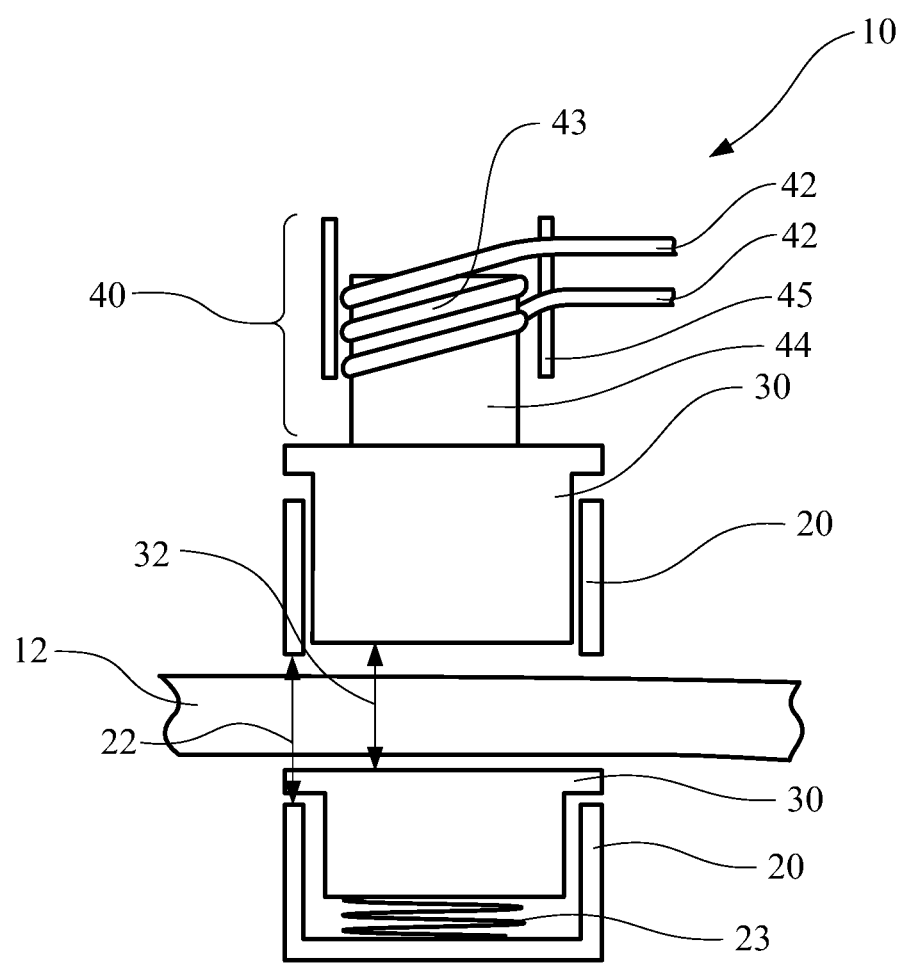
FIG. 3 shows a partially cut away view of the automatic safety occluder of FIG. 1 in its active open condition.

Turning now to FIG. 3, a cut away view of the occluder 10 in an open position is shown. An electrical signal is applied to the solenoid 40 via wires 42, causing an electromagnetic field within the solenoid to extend the piston 44 and thereby press on the plunger 30 and overcome the bias of the spring 23. The plunger 30 moves relative to the body 20 such that the plunger aperture 32 lines up with the body aperture 22. The occluder 10 no longer pinches the tubing 12, allowing flow through the tubing.

Figure 4:
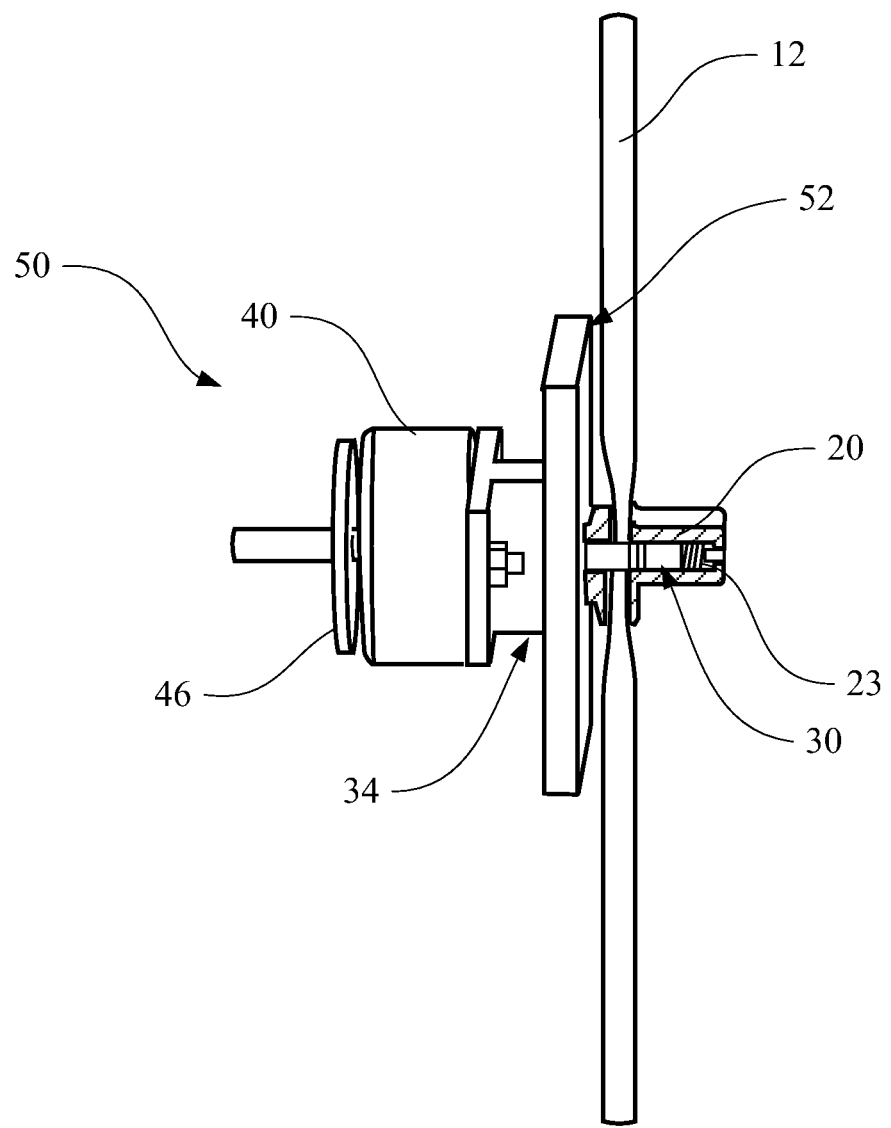
FIG. 4 shows a perspective view of another automatic safety occluder.

Turning now to FIG. 4, a perspective view of another occluder and solenoid, designated generally at 50, is shown. The occluder 50 accepts a tubing 12 and functions in a manner similar to that discussed above to selectively allow or prevent flow through the tubing. The occluder 50 includes a registration member 52 which aids in the positioning of the body 20 relative to the solenoid 40, tubing 12, and plunger 30. Additionally, the registration member 52 may be designed to aid in properly loading the occluder 50 into a pump 60. In such a case, the registration member would match an opening in the pump or otherwise physically engage the pump body. The solenoid 40 and associated members (40, 46, 34, 52, 33) can be built into the pump 60 so that it is permanently attached to the pump. In such a design, the registration member 52 may include structures to ensure proper alignment of the solenoid 40 with the occluder body 20, such as a recess in the registration member 52 which receives a projection on the solenoid 40. The occluder body 20, plunger 30, and spring 23 typically are permanently attached to the tubing 12 and make up part of the disposable tubing set. The plunger 30 is biased in the closed position by a return spring 23 mounted within a spring housing 34.

As shown, the solenoid 40 interfaces with the body 20 and plunger 30. An occluder unit as shown has the advantages of a reduced risk of alignment error between the body 20, plunger 30 and solenoid 40, and reduced risk of misalignment within a pump.

Figure 5:
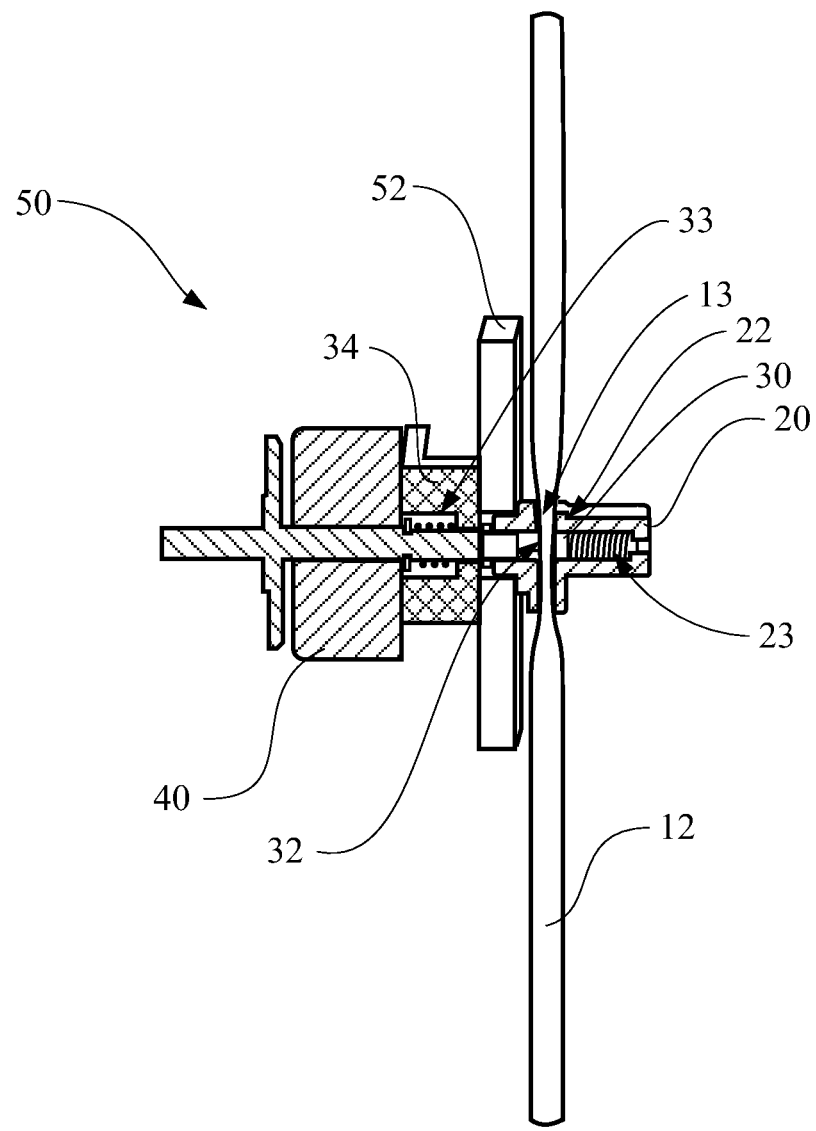
FIG. 5 shows a cut-away view of the automatic safety occluder of FIG. 4 in its biased closed condition.

Turning now to FIG. 5, a partially cut-away view of the occluder 50 of FIG. 4 is shown. The occluder 50 is shown in its biased closed condition. The return spring 23 pushes the plunger 30 such that it pinches the tubing 12 between the edges of the body aperture 22 and the plunger aperture 32. The bias caused by the plunger return spring 23 and the solenoid return spring 33 ensures that whether or not the solenoid is actively driven closed, the occluder 50 will remain in a closed position to prevent free flow through the tubing lumen 13 absent an affirmative electrical signal to open the occluder 50.

Figure 6:
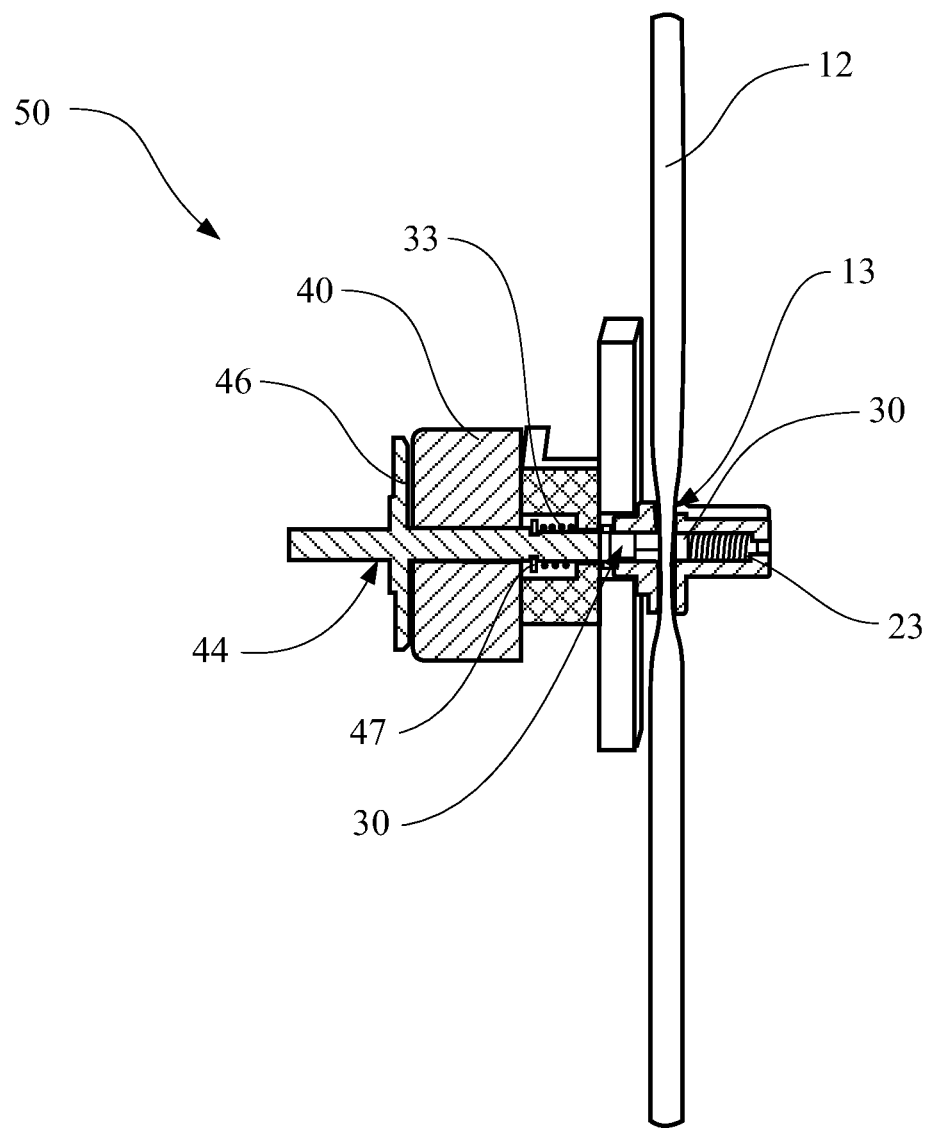
FIG. 6 shows a cut-away view of the automatic safety occluder of FIG. 4 in its active open condition.

Turning now to FIG. 6, a cut-away view of the occluder 50 of FIG. 4 is shown. The occluder 50 is shown in its active open condition. When the solenoid 40 receives an electrical signal to open, the solenoid applies a force with the piston 44 to the plunger 30 which is higher that the force applied by the return spring 23. The plunger 30 moves to release the tubing 12 and allow flow through the tubing lumen, indicated at 13. In one embodiment, the movement of the solenoid piston 44 is limited by an upper ring 46 and a lower ring 47 connected to the piston 44. As shown, the lower ring 47 provides both a positive stop for the plunger 30 and a stop against which the spring 33 pushes to restore the solenoid to a non-actuating position.

Figure 7:
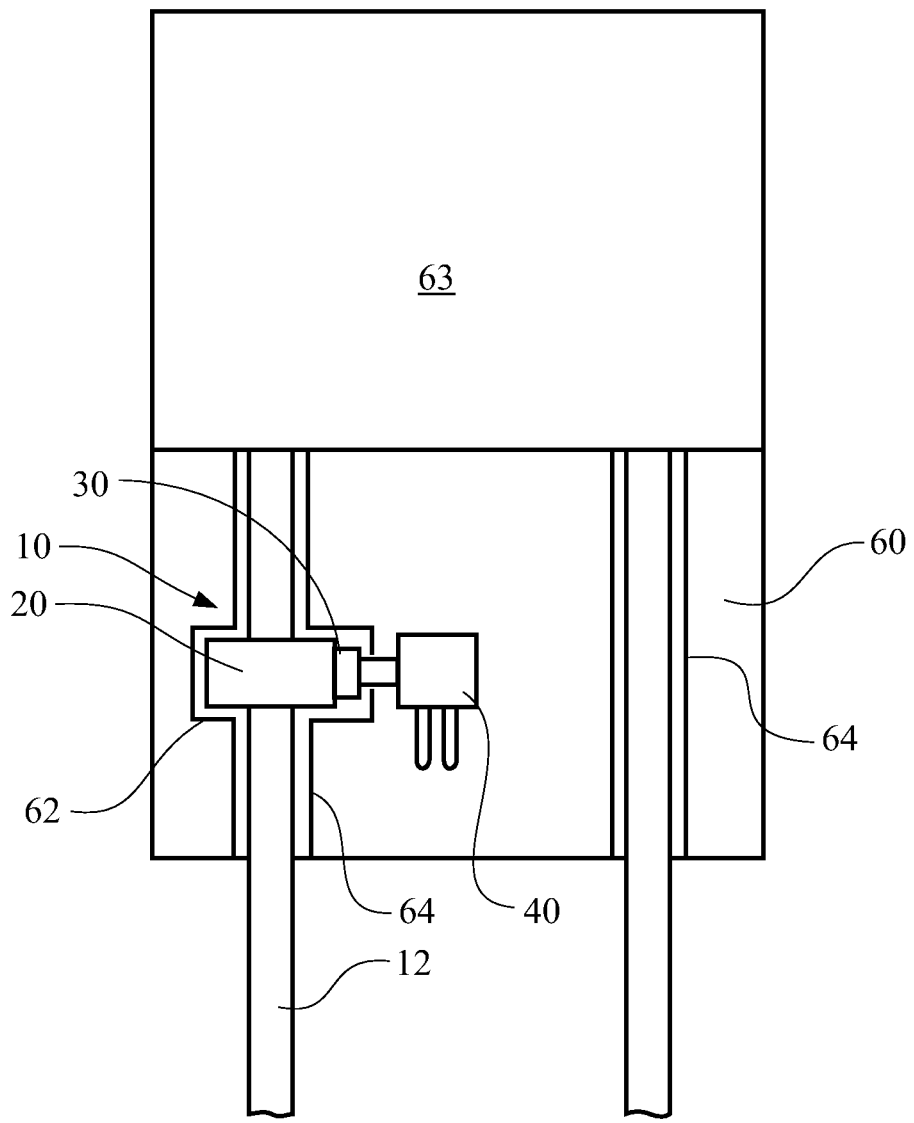
FIG. 7 shows a diagram of the automatic safety occluder of FIGS. 1 and 4 and an infusion set loaded into a pump.

Turning now to FIG. 7, a schematic diagram of an occluder 10 in an infusion pump 60 is shown. The body 20 and plunger 30 are located on tubing 12 as part of an infusion set. The tubing 12 is loaded into the pumping head 63. Where the solenoid 40 is formed as part of the pump 60 separate from the occluder 10, the occluder 10 is placed within a recess 62 in the pump body that places the body 20 and plunger 30 in contact with the solenoid 40. As discussed, a registration member 52 may be used to ensure alignment of the occluder 10 with the pump 60 and with the solenoid 40. Where the solenoid 40 is integrated into the occluder 10, the body 20, plunger 30, and solenoid 40 are placed within the recess 62. The solenoid 40 is electrically connected to the pump 60 such that the pump can control the occluder 10 via solenoid 40. The tubing 12 is placed inside of a channel 64.

The solenoid driven occluder 10 provides many advantages over the prior art occluders. Should a pump failure or other error occur, the pump 60 may automatically cut power to the solenoid 40 and thereby close the occluder 10. Similarly, if system power is lost, the occluder 10 will automatically be closed, since any loss of power to the solenoid 40 will cause the occluder to return to its closed bias and will prevent further fluid flow. If the tubing 12 and occluder 10 are accidentally removed from the pump 60, the occluder 10 will automatically be closed whether or not electrical power is removed form the solenoid 40. Without force from the solenoid 40 to overcome the bias, the body 20 and plunger 30 will forced into a biased closed state. The use of an electric solenoid 40 to control the occluder 10 allows the occluder to function as a flow control device, rather than simply an anti-freeflow device.

The automatic safety occluder 10 may be configured to work with different pumps. These may include peristaltic pumps, finger pumps, infusion or syringe pumps, or other methods of moving liquids through tubing.

There is thus disclosed an improved automatic safety occluder. It will be appreciated that numerous changes may be made to the present invention without departing from the scope of the claims.

What is claimed is:

1. A method of selectively preventing flow through an infusion set comprising:
   selecting an infusion set, the infusion set having a tube through which fluid is delivered and an occluder disposed on the tube;
   selecting a pump, the pump having an electric solenoid;
   mounting the infusion set and occluder in a pump such that the occluder is disposed adjacent the solenoid; and
   selectively sending an electrical signal to the occluder to selectively allow flow through the occluder.

2. The method of claim 1, wherein the pump has a recess therein for receiving the occluder and wherein the solenoid is disposed in communication with the recess.

3. The method of claim 1, wherein the method comprises selecting an infusion set with an occluder comprising:
   a body having a passage therethrough;
   a plunger movable within the body and having a passage therethrough;

the tube located in the body passage and the plunger passage;

wherein the plunger is movable between a first position wherein the body passage and the plunger passage are in alignment to allow flow through the tube and a second position wherein the tube is pinched between the body passage and the plunger passage; and a biasing member disposed between the body and the plunger to bias the plunger into the second position.

\* \* \* \* \*